United States Patent [19]

Sagaye et al.

[11] Patent Number: 5,171,383
[45] Date of Patent: Dec. 15, 1992

[54] METHOD OF MANUFACTURING A DIFFERENTIALLY HEAT TREATED CATHETER GUIDE WIRE

[75] Inventors: Kyuta Sagae; Yoshiaki Sugiyama, both of Fuji, Japan

[73] Assignee: Terumo Kabushiki Kaisha, Tokyo, Japan

[21] Appl. No.: 760,813

[22] Filed: Sep. 16, 1991

Related U.S. Application Data

[60] Division of Ser. No. 657,895, Feb. 19, 1991, abandoned, which is a continuation of Ser. No. 381,391, Jul. 5, 1989, abandoned.

Foreign Application Priority Data

Jan. 7, 1987 [JP] Japan .................................. 62-1468

[51] Int. Cl.$^5$ .................. C12D 8/06; A61M 23/00
[52] U.S. Cl. .................. 148/564; 148/563; 148/676; 148/902; 604/282; 128/772
[58] Field of Search .............. 148/402, 13, 563, 564, 148/676; 128/902, 657, 772; 604/95, 164, 170, 280, 282

[56] References Cited

U.S. PATENT DOCUMENTS

| | | | |
|---|---|---|---|
| 3,789,841 | 2/1974 | Antoshkiw | 128/772 |
| 3,906,938 | 9/1975 | Fleischhacker | 128/772 |
| 4,484,955 | 11/1984 | Hochstein | 148/402 |
| 4,943,326 | 6/1990 | Ozawa et al. | 420/902 |

FOREIGN PATENT DOCUMENTS

| | | | |
|---|---|---|---|
| 0141006 | 5/1985 | European Pat. Off. | 128/772 |
| 59-48643 | 3/1984 | Japan . | |
| 0219443 | 12/1984 | Japan | 148/402 |
| 60-63066 | 4/1985 | Japan . | |
| 8501444 | 4/1985 | World Int. Prop. O. | 128/772 |

OTHER PUBLICATIONS

Derwint Abs. C85-008892 (of Japan 59-215447) 1985.
Derwint Abs. C85-008891 (of Japan 59-215447) 1985.

*Primary Examiner*—R. Dean
*Assistant Examiner*—Margery S. Phipps
*Attorney, Agent, or Firm*—Frishauf, Holtz, Goodman & Woodward

[57] ABSTRACT

A catheter guide wire is provided for guiding a catheter into a body cavity such as a blood vessel. The base material constituting the wire is made of an elastic alloy wire and subjected to a heat treatment such that its flexibility is sequentially increased from its proximal to distal end portions. A thermoplastic resin or/and a coil spring can be applied to at least the distal end portion of the wire base material. A method of manufacturing the catheter guide wire is also provided. The method is characterized in that the leading end side of the base material is divided into a plurality of areas and subjected to a heat treatment by changing the heat treatment temperature and the time conditions in units of the areas so that the flexibility of the base material is sequentially increased from the proximal to distal end portions of the leading end side.

4 Claims, 2 Drawing Sheets

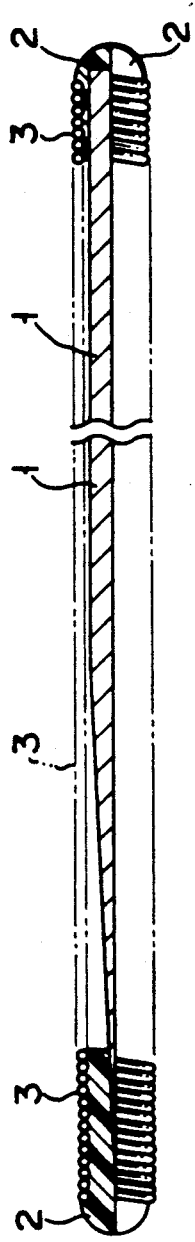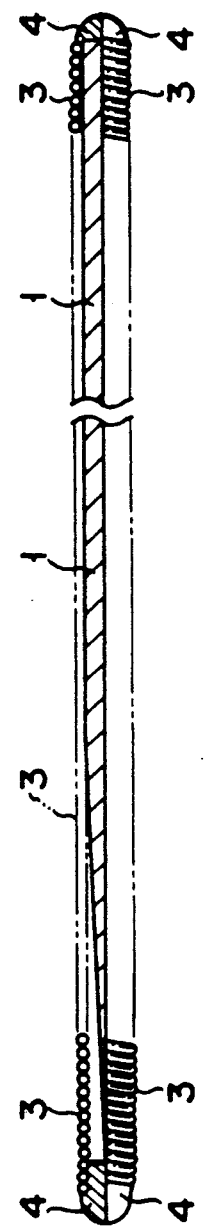
FIG. 3
FIG. 4

METHOD OF MANUFACTURING A DIFFERENTIALLY HEAT TREATED CATHETER GUIDE WIRE

This application is a division of application Ser. No. 07/657,895, filed Feb. 19, 1991, now abandoned, which is a continuation of Ser. No. 07/381,391 filed Jul. 5, 1989, now abandoned.

TECHNICAL FIELD

The present invention relates to a catheter guide wire for guiding a clinical or testing catheter to a predetermined portion of a body cavity such as a blood vessel, a digestive tract, and a windpipe and holding it therein, and a method of manufacturing the same.

PRIOR ART

When a catheter is to be guided to a branching peripheral portion of a blood vessel or the like, first, a guide wire must be guided to a target portion. In this case, since a target portion is generally thin and thus tends to be easily damaged, the distal end portion of the guide wire must be flexible so that it will not damage a blood vessel wall, will follow the shape of the blood vessel well even if the blood vessel is curved, and can be inserted in a complex branching blood vessel. Meanwhile, the proximal end portion of the guide wire must have torque transmitting performance so that a manual operation performed at the proximal end portion is transmitted to the distal end portion. Thus, the proximal end portion of the guide wire must have comparatively high rigidity.

According to a conventional catheter guide wire having the above characteristics, a coil guide wire is made of a stainless steel wire or a piano wire, or a guide wire is made of a plastic monofilament. In each of these guide wires, its sectional area is decreased from its proximal to distal end portion, and the guide wire forms a main portion having relatively high rigidity and a relatively flexible distal end portion.

However, plastic deformation can easily occur in these conventional guide wires, and some manual operation can kink the guide wires. A kinked portion becomes an obstacle during introduction of a catheter, thus rendering smooth introduction operation of a catheter impossible as well as greatly degrading its torque transmitting performance.

A catheter guide wire free from such kinking deformation uses a very elastic alloy (e.g., Ni-Ti alloy) as a core member (see Japanese Patent Disclosure (Kokai) No. 60-63066).

A guide wire using a very elastic alloy is flexible and can restore its original shape after it is deformed to a considerable degree (strain of about 8%). Therefore, such a guide wire cannot be easily broken during operation and will not easily attain a bending tendency. However, such guide wire has a high elasticity at its distal end portion and is thus infavorable in terms of flexibility. Then the diameter of its proximal end portion is 0.5 mm or less, the rigidity is insufficient and the torque transmitting performance is poor.

DISCLOSURE OF THE INVENTION

The present invention has been made in view of the above situation and has as its object to provide a catheter guide wire wherein its distal end portion is very flexible, buckling deformation is difficult to occur, and its proximal end portion is very rigid, thus having a good torque transmitting performance to the distal end portion, and a method of manufacturing the same.

In order to solve the above problems, according to the present invention, a wire member made of an elastic alloy, and preferably a very elastic alloy, is used as a core member of a catheter guide wire and subjected to a heat treatment by changing the treatment conditions along its longitudinal direction, so that the rigidity at its proximal end portion becomes comparatively high, the flexibility at its distal end portion is increased, and kinking deformation will not easily occur in its distal end portion.

More specifically, according to the present invention, there is provided a catheter guide wire having leading and trailing end sides, characterized in that the guide wire comprises a wire member made of an elastic alloy member, at least the leading end side thereof has an outer diameter equal to or smaller than a minimum inner diameter of a catheter, and the wire member is subjected to a heat treatment so that its flexibility is sequentially increased from a proximal to distal end portion of the leading end side thereof.

Note that the catheter guide wire can be fabricated by using as a core member a wire member made of an elastic alloy member subjected to the heat treatment described above and forming a cover layer of a thermoplastic resin on the core member.

The core member preferably uses a very elastic alloy such as an Ni-Ti alloy, a Cu-Zn-Al alloy, a Cu-Al-Ni alloy, and an Fe-Mn alloy. The core member is preferably tapered such that a diameter at its distal end portion is smaller than that at its proximal end portion. A contrast medium such as a tungsten powder can be added to the thermoplastic resin layer.

A flexible coil spring having an outer diameter equal to or smaller than a minimum inner diameter of the catheter can be mounted to surround at least the distal end portion of the wire member.

In this case, the coil spring is preferably made of a material having a high X-ray impermeability in order to allow an X-ray photographing to be easily confirmed. Therefore, the presence of the coil spring is advantageous in giving a sufficient thickness in an X-ray image without badly affecting the flexibility of the guide wire.

As a result, the coil spring is made of a material selected from a group consisting of stainless steel, platinum, a platinum alloy and a palladium alloy, and preferably has a thickness of 0.01 to 0.15 mm, more preferably 0.05 to 0.1 mm.

Furthermore, according to the present invention, there is provided a method of manufacturing a catheter guide wire fabricated by using an elastic alloy wire as a base material, characterized in that a leading end side of the base material is divided into a plurality of areas, and a heat treatment is performed by changing the temperatures and time in units of the areas so that the flexibility of the base material is sequentially increased from the proximal to distal end portion of the leading end side.

In a conventional catheter guide wire, a diameter at a proximal end portion of a wire member made of an elastic alloy or a very elastic alloy is merely increased, and a diameter at its distal end portion is relatively decreased, thereby making the proximal end portion rigid and the distal end portion flexible. Unlike such a conventional catheter guide wire, according to the present invention, a wire member is subjected to a heat treatment by sequentially changing the confunction along its longitudinal direction. As a result, the physical characteristics of the wire member can be set in an ideal state as a catheter guide wire.

BRIEF DESCRIPTION OF THE DRAWINGS

FIGS. 3 and 4 respectively represent a sectional view of a catheter guide wire on which a coil spring is mounted according to another embodiment of the present invention.

BEST MODE FOR CARRYING OUT THE INVENTION

Preferred embodiments of the present invention will be described with reference to the accompanying drawings.

Figure 1:
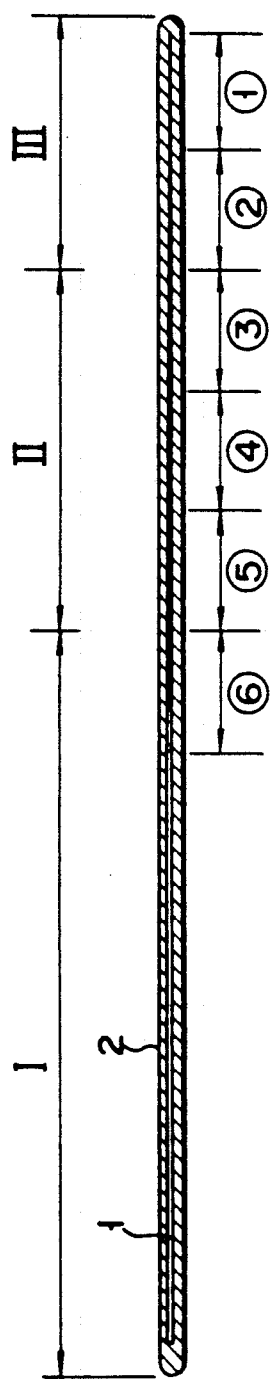
FIG. 1 is a sectional view of a catheter guide wire according to an embodiment of the present invention.

FIG. 1 is a sectional view of a catheter guide wire taken along the longitudinal direction according to an embodiment of the present invention. Referring to FIG. 1, reference numeral 1 denotes a core member; and 2, a thermoplastic resin layer entirely covering core member 1.

Core member 1 is a wire member made of an elastic alloy wire such as a piano wire, and preferably a very elastic alloy such as an Ni-Ti alloy. Core member 1 can have a uniform diameter of 0.2 to 0.4 mm, or can be tapered toward its distal end such that the diameter at its proximal end portion is 0.2 to 0.4 mm and the diameter at its distal end portion is 0.01 to 0.1 mm. In this specification, a very elastic alloy is defined as an alloy whose recoverable elastic strain is as large as several % to more than ten % and whose stress level does not exceed a predetermined value even if the strain is increased. The very elastic alloy generally comprises an Ni-Ti, Cu-Zn-Al, Cu-Al-Ni, or Fe-Mn alloy. If an Ni-Ti alloy is employed, it preferably contains 49 to 58 atm. % of Ni and a balance of Ti, and more preferably 49 to 51 atm. % of Ni and a balance of Ti. If a Cu-Zn-Al alloy is employed, it preferably contains 38.5 to 41.5 wt. % of Zn, 1 to 10 wt. % of ADP, and a balance of Cu. If a Cu-Al-Ni alloy is employed, it preferably contains 14 to 14.5 wt. % of Al, 3 to 4.5 wt. % of Ni, and a balance of Cu. If an Fe-Mn alloy is employed, it preferably contains 28 to 32 wt. % of Mn, 6 wt. % of Si, and a balance of Fe. A heat treatment is performed by changing the treatment conditions. As a result, the guide wire can have the following physical characteristics in its areas (1) to (III) as shown in FIG. 1.

(1) Proximal end portion (I)

When the guide wire is guided from, e.g., a straight great blood vessel (e.g., a descending aorta) to an arteriole (e.g., a coronary artery), proximal end a comparatively small number of bent portions. Proximal and portion (I) has a comparatively high rigidity and is difficult to deform. Therefore, forward/backward movement and rotation externally applied to the catheter can be easily transmitted to the distal end portion (II—III) through a blood vessel retaining an introducer (not shown).

(2) Intermediate portion (II)

Intermediate portion (II) has an elasticity so that it can easily follow a blood vessel curve of a comparatively large curve and can return to its initial shape when deformation caused by the curve is removed. Although it is flexible, intermediate portion (II) hardly attains a bending tendency and is difficult to break.

(3) Distal end portion (III)

When distal end portion (III) is inserted in a small, curved blood vessel, it can easily follow the blood vessel shape due to its flexibility, and thus will not damage the blood vessel wall. When a blood vessel has phatologic factor such as arteriosclerosis, the flexibility of distal end portion (III) is important.

Thermoplastic resin layer 2 is provided as needed in order to protect the inner surface of the blood vessel, to prevent formation of thrombus on an outer surface of the guide wire during operation of the guide wire, and not to form a difference in outer diameter between the proxital end portion and the distal end portion. For example, saturated aliphatic polyether urethane is used to form layer 2. A contrast medium can be mixed in the thermoplastic resin in advance in order to increase the contrast of the guide wire through X-ray photographing. For example, 40 to 600 parts by weight (with respect to 100 parts by weight of thermoplastic resin) of a tungsten powder can be mixed as the contrast medium. Note that saturated aliphatic polyether polyurethane is favorable for compounding of tungsten.

Figure 2:
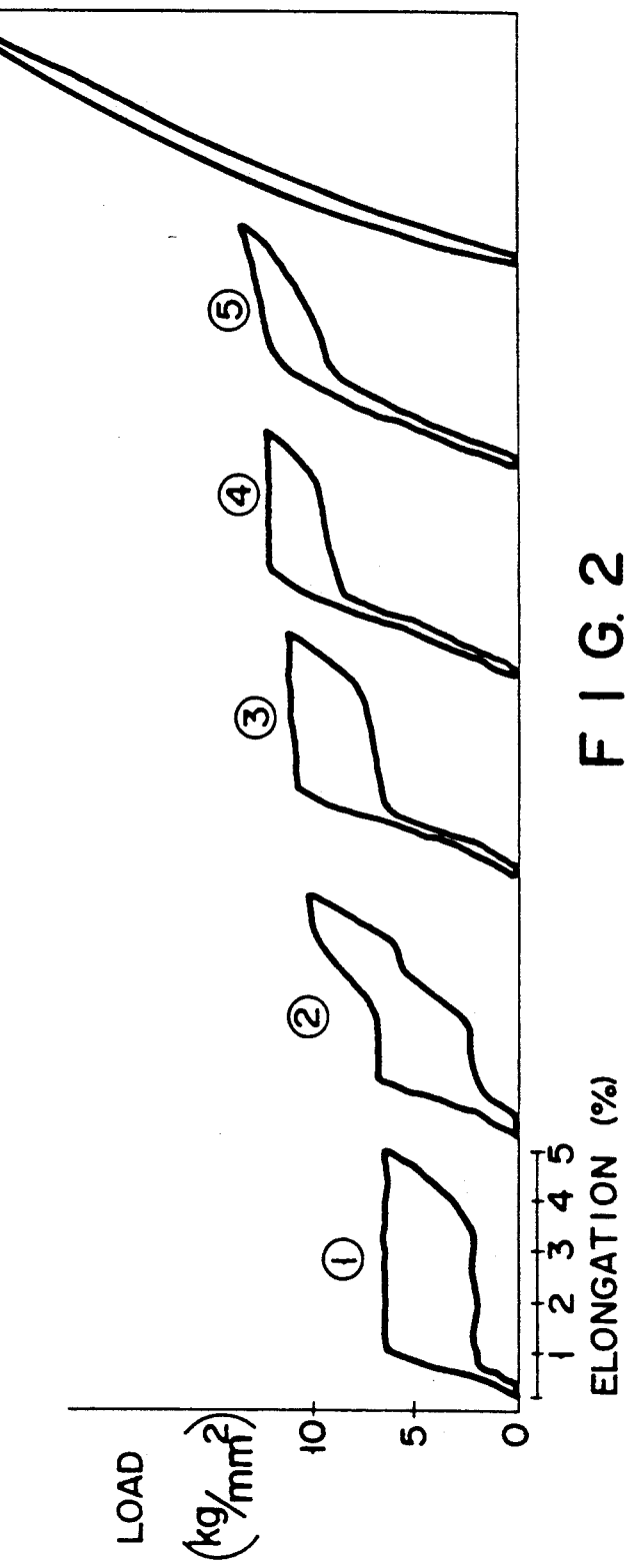
FIG. 2 is a graph of strain-stress curves of the core member of the guide wire according to the embodiment of the present invention.

FIG. 2 shows the physical characteristics (strain-stress curve) at the respective portions of the core member of the present invention after a heat treatment. A heat treatment can be performed in an atmosphere of an inert gas (Ar or He), vacuum ($\times 10$-2 Torr or less) or outer atmosphere. Although a heat treatment can be performed in an outer atmosphere, it is preferably performed in a vacuum in view of embrittlement of the material, and more preferably in an inert gas. The values in FIG. 2 are obtained by cutting the core member sample into 70-mm long pieces starting from its distal end and subjecting the respective samples to a tension test.

Core member: Ni-Ti alloy wire (diameter: 0.4 mm) (49 atm. % of Ni and a balance of Ti)

Heat treatment conditions:

| Area of Guide Wire | Heat Treatment Conditions | Tension Test Sample No. |
|---|---|---|
| Distal end portion (III) | About 2 hrs. at 400 to 500° C. and about 24 hrs. at 200° C. (in outer atmosphere) | (1) (2) |
| Intermediate portion (II) | About 2 hrs. at 400 to 500° C. (in outer atmosphere) | (3) (4) (5) |
| Proximal end portion (I) | No heat treatment after cold rolling | (6) |

The physical characteristics at the respective portions of core member 1 are not limited to those shown in FIG. 2 and can be arbitrarily adjusted and selected in accordance with specific applications.

FIG. 3 is a partial sectional view of a catheter guide wire according to another embodiment of the present invention. Thermoplastic resin layer 2 is formed on the entire surface of core member 1 in the same manner as in FIG. 1, and coil spring 3 having a thickness of 0.08 mm is mounted on an outer surface of resin layer 2 excluding its leading and trailing end faces. Note that coil spring 3 may be provided at only the distal end portion of the guide wire. The outer diameter of the guide wire may be conveniently selected to conform with the inner diameter of a blood vessel to be inserted. Generally, however, the outer diameter of the guide wire may be selected within a range of from 0.2 to 2.0 mm.

When coil spring 3 is applied on resin layer 2 in this manner, the physical characteristics of the guide wire are as flexible at its distal end portion as shown in FIG. 1 and highly resistive to buckling deformation due to the high flexibility of the coil spring 3, relatively high in rigidity at its proximal end portion and excellent in X-ray photographing.

Coil spring 3 can be provided to directly surround core member 1 without intervening thermoplastic resin layer 2.

FIG. 4 shows an example of such a structure of the guide wire, wherein the coil spring 3 is directly wound around the outer wall of core member 1, with its distal and proximal end portions being fixed to core member 1 through a soldering material 4 made for example of Sn-Ag (96:4) alloy.

As described above, according to the catheter guide wire of the present invention, a wire member made of an elastic alloy is used as a core member and subjected to a heat treatment by sequentially changing the treatment conditions along its longitudinal direction. As a result, the proximal end portion of the guide wire has predetermined rigidity required in accordance with its application, and its distal end portion has predetermined flexibility.

Industrial Application

The guide wire as proposed by this invention is useful for guiding a clinical or testing catheter to a predetermined portion of a body cavity such as blood vessel, a digestive tract and a windpipe, and holding it therein for a period of time.

We claim:

1. A method of making a catheter guide wire for guiding a catheter, said method comprising:
    forming a wire member comprising a superelastic Ni-Ti alloy wire as a base material, said base material having a proximal end portion and a leading end side;
    dividing said leading end side of said base material into a plurality of areas along the length thereof and a distal end portion, said plurality of areas comprising an intermediate portion between said proximal and distal end portions; and
    subjecting only said intermediate portion and said distal end portion to a primary heat treatment at a temperature of 400° to 500° C. for about two hours, and then subjecting only said distal end portion to a secondary heat treatment at a temperature of about 200° C. for about 24 hours, whereby said proximal end portion is not heat treated after cold rolling, such that said distal end portion, after said primary and secondary heat treatments, has a yield stress of approximately 5 to 7 kg/mm$^2$, and at least one of said areas at said intermediate portion, after said heat treatment, has a yield stress of approximately 11 to 12 kg/mm$^2$.

2. A method according to claim 1, comprising forming said wire member so as to have a proximal end portion having an outer diameter ranging from 0.2 to 0.4 mm.

3. A method of making a catheter guide wire for guiding a catheter, said method comprising:
    forming a wire member comprising a superelastic Ni-Ti alloy wire as a base material, said base material having a proximal end portion and a leading end side;
    dividing said leading end side of said base material into a plurality of areas along the length thereof and a distal end portion, said plurality of areas comprising an intermediate portion between said proximal and distal end portions; and
    subjecting only said intermediate portion and said distal end portion to a primary heat treatment at a temperature of 400° to 500° C. for about two hours, and thereafter subjecting only said distal end portion to a secondary heat treatment at a temperature of about 200° C. for about 24 hours, whereby said proximal end portion is not heat treated after cold rolling, such that, after said primary and secondary heat treatments, flexibility of the guide wire is increased from said proximal end portion to said distal end portion thereof.

4. A method according to claim 3, comprising forming said wire member so as to have a proximal end portion having an outer diameter ranging from 0.2 to 0.4 mm.

* * * * *

UNITED STATES PATENT AND TRADEMARK OFFICE
CERTIFICATE OF CORRECTION

PATENT NO. : 5,171,383
DATED : December 15, 1992
INVENTOR(S) : SAGAE ET AL It is certified that error appears in the above-identified patent and that said Letters Patent is hereby corrected as shown below:

Title page:

Line 2 (left column) under "United States Patent [19]", change "Sagaye et al" to --Sagae et al--.

In Section [30] under "Foreign Application Priority Data", insert --PCT/JP87/01031 - December 25, 1987--.

In Section [56] under "References Cited", change the corresponding Japanese reference of Derwent Abs. C85-008892 from "59-215447" to --59-215448--.

Signed and Sealed this

Seventh Day of December, 1993

*Attest:*

BRUCE LEHMAN

*Attesting Officer*    Commissioner of Patents and Trademarks